US00PP29413P2

(12) United States Plant Patent
Van Dijk

(10) Patent No.: US PP29,413 P2
(45) Date of Patent: Jun. 19, 2018

(54) ***ANTHURIUM* PLANT NAMED 'ANTHEVEX'**

(50) Latin Name: ***Anthurium andreanum* L.**
Varietal Denomination: ANTHEVEX

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days. days.

(21) Appl. No.: 15/731,216

(22) Filed: May 3, 2017

(51) Int. Cl.
*A01H 5/02* (2018.01)

(52) U.S. Cl.
USPC ..... Plt./368
CPC ..... *A01H 5/02* (2013.01)

(58) Field of Classification Search
USPC ..... Plt./368
CPC ..... A01H 5/02
See application file for complete search history.

*Primary Examiner* — Kent L Bell
(74) *Attorney, Agent, or Firm* — Jondle & Associates, P.C.

(57) ABSTRACT

A new *Anthurium* plant named 'ANTHEVEX' particularly distinguished by having small, shiny, purple, long-ovate and durable spathes that retain the original color for a very long period of time, green, shiny and long-ovate, durable leaves, purple spadix, early flowering continuously throughout the year and a plant height of 20.0 cm to 25.0 cm, is disclosed.

3 Drawing Sheets

Genus and species: *Anthurium andreanum* L.
Variety denomination: 'ANTHEVEX'.

BACKGROUND OF THE NEW PLANT

The present invention comprises a new and distinct variety of *Anthurium*, botanically known as *Anthurium andreanum* L., and hereinafter referred to by the variety name 'ANTHEVEX'. The new *Anthurium* plant is a product of a planned breeding program conducted by the inventor in Bleiswijk, The Netherlands. The objective of this breeding program was to create a new plant with small, shiny, purple and long-ovate spathes.

The new variety originated from a cross-pollination made in November 2008 in Bleiswijk, The Netherlands. The female parent was a purple *Anthurium* pot plant designated 'ANTHUCOEN' (U.S. Plant Pat. No. 22,630), and the male parent was a purple *Anthurium* pot plant designated '10441-14' (unpatented).

A single plant was selected from the progeny of the stated cross in September 2010 and has been asexually reproduced repeatedly by tissue culture in Bleiswijk, The Netherlands over a 4-year period. The present invention has been found to retain its distinctive characteristics through successive asexual propagations.

Plant Breeder's Rights for this variety have been applied for in the European Union on Nov. 24, 2015. 'ANTHEVEX' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Small, shiny, purple and long-ovate spathe;
2) Purple spadix; and
3) Green, shiny and long-ovate leaves.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 34-week old plant grown in a greenhouse in Bleiswijk, The Netherlands in March 2017. Colors in the photographs may differ from the color values cited in the detailed botanical description, which accurately describe the actual colors of the new variety.

DESCRIPTION OF THE NEW VARIETY

Figure 1:
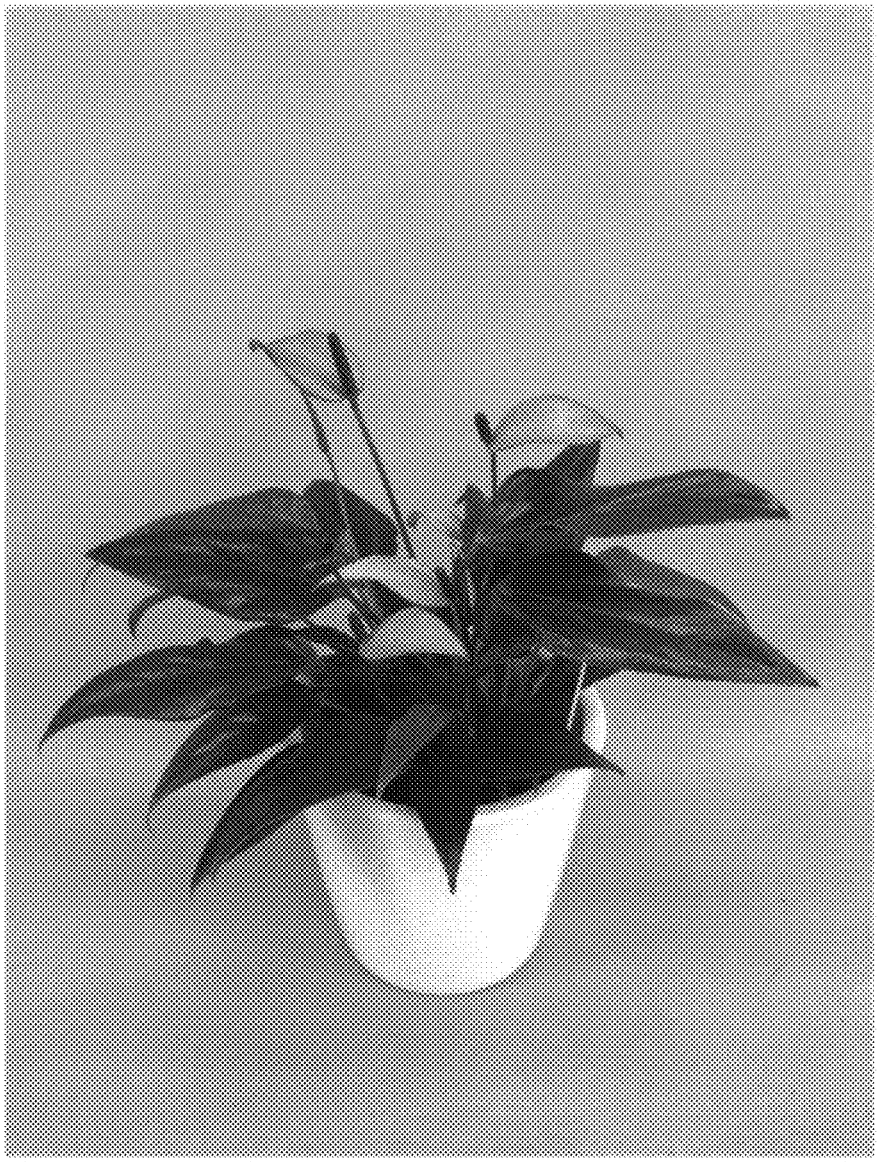
FIG. 1 shows the overall plant habit, including blooms, buds and foliage.
Figure 2:
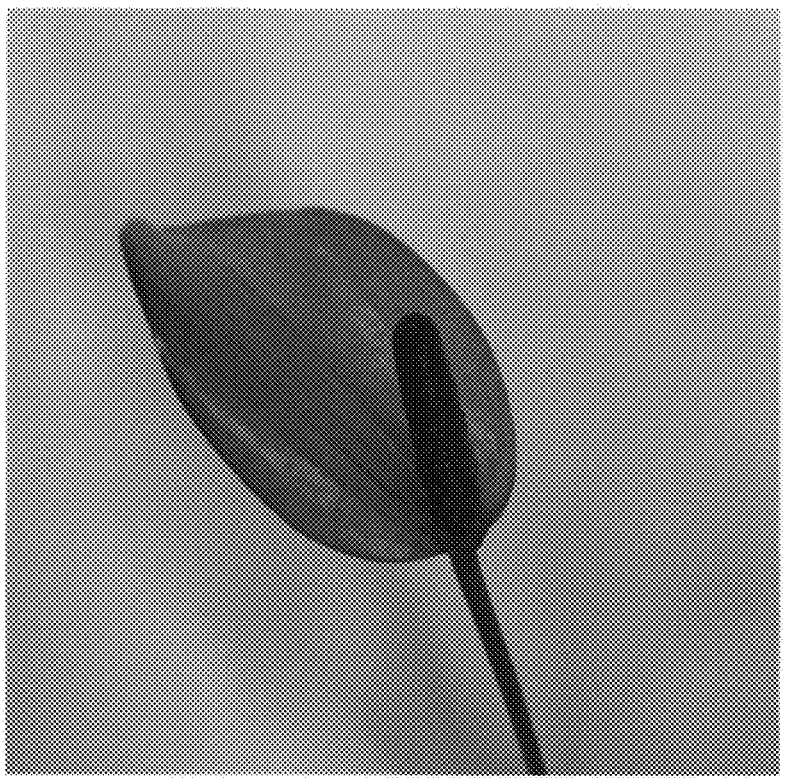
FIG. 2 shows a close-up of the mature spathe.
Figure 3:
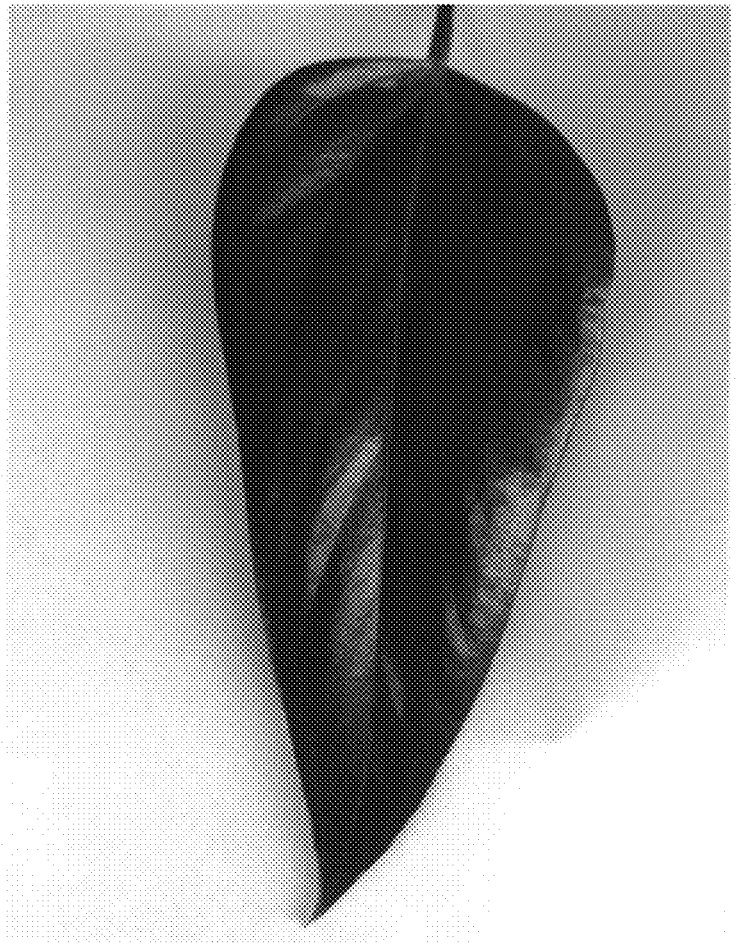
FIG. 3 shows a close-up of the upper leaf blade surface.

The following detailed description sets forth the distinctive characteristics of 'ANTHEVEX'. The data which define these characteristics were collected from asexual reproductions carried out in Bleiswijk, The Netherlands. The plant history was taken on 34-week old plants which were planted from tissue culture in 12-centimeter (diameter) pots and grown in a glass greenhouse between 19° C. and 24° C. Observations were made in March 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.
*Botanical*.—*Anthurium andreanum* L.
*Common name*.—*Anthurium*.
*Denomination*.—'ANTHEVEX'.

Parentage:

*Female parent.*—*Anthurium* plant 'ANTHUCOEN' (U.S. Plant Pat. No. 22,630).

*Male parent.*—*Anthurium* plant '10441-14' (unpatented).

Plant:

*Propagation.*—Tissue culture.

*Root description.*—Fleshy-creamy colored roots with small hairy lateral roots having yellow colored root tips.

*Time to produce a finished flowering plant.*—32 to 36 weeks after planting in a 12 cm (diameter) pot.

*Growth habit.*—Herbaceous perennial.

*Height (measured from soil, including inflorescence).*—20.0 cm to 25.0 cm.

*Width (measured from leaf tips).*—29.0 cm to 34.0 cm.

Leaves:

*Immature leaves.*—Length: 9.0 cm to 12.0 cm. Width: 4.0 cm to 5.0 cm. Color: Upper surface: RHS 146A. Lower surface: RHS 146B. Texture (both upper and lower surfaces): Shiny.

*Mature leaves.*—Length (fully expanded): 12.0 cm to 14.0 cm. Width: 6.0 cm to 7.0 cm. Shape: Long-ovate. Apex: Acuminate. Base: Rotundate. Leaf blade angle with the petiole: Between 125 degrees and 135 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes.*—Absent.

*Petiole.*—Cross-section: Round. Diameter: 0.2 cm to 0.3 cm. Length: 8.0 cm to 9.0 cm for a mature leaf size. Color: Mature leaf: RHS 144A. Immature leaf: RHS 144B. Cataphyll color surrounding the petiole: Outside: RHS 145B. Inside: RHS 145C.

*Geniculum.*—Length: 1.5 cm to 1.9 cm. Width: 0.3 cm to 0.4 cm. Color: RHS 146B and RHS 176B.

Inflorescence:

*Arrangement.*—Single.

*Flowering habit (length of flowering season).*—Continuous.

*Number of inflorescences per plant.*—7 to 9.

*Fragrance.*—Absent.

*Longevity of inflorescence on plant.*—Over half a year.

Spathe:

*Buds.*—The spathe is tightly rolled around the spadix and extrudes from the peduncle sheath. After the spathe is fully open, the peduncle elongates some extra centimeters.

*Arrangement.*—Spathe angle with the peduncle is between 120 degrees and 135 degrees; the spathe stands on a wiry peduncle about 6.0 cm to 8.0 cm above the foliage.

*Shape.*—Long-ovate.

*Apex.*—Acuminate.

*Base.*—Ovate.

*Texture.*—Shiny.

*Margin.*—Entire.

*Size.*—Length: 5.5 cm to 6.5 cm. Width: 2.5 cm to 3.5 cm.

*Lobes.*—Absent.

*Color.*—Just fully open: Upper surface: RHS N77B. Lower surface: RHS N77D. Ages to: RHS 55C. This purple color remains for a very long period, at least more than 30 weeks after opening.

Peduncle:

*Shape.*—Erect.

*Cross-section.*—Round.

*Length.*—16.0 cm to 18.0 cm.

*Diameter.*—0.2 cm to 0.3 cm.

*Color.*—RHS 144A and toward the spathe RHS 187D.

Flowering time:

*General.*—One small rooted untreated tissue culture plant of 8.0 cm tall will flower, depending on season, after 32 to 34 weeks and 6 to 7 blossoms appear. More blossoms appear after some additional weeks so that a full flowering and commercial plant will have 7 to 9 purple spathes. Smaller blossoms may occur on immature plants.

Spadix:

*Size.*—Length: 2.0 cm to 3.0 cm (depending on flower size). Width (at apex): 0.4 cm to 0.5 cm. Width (at base): 0.4 cm to 0.5 cm.

*Shape.*—Columnar.

*Angle from spadix tip to peduncle.*—170 degrees to 180 degrees.

*Texture.*—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color.*—Immature: RHS N79A. Mature: RHS N79B. Ages to: RHS N79A.

Flowers:

*Quantity per spadix.*—80 to 120.

*Spadix flower arrangement.*—Bisexual, rounded in cross-section.

*Shape.*—Rounded.

*Size.*—Length: 0.05 cm to 0.10 cm. Diameter (maximum): 0.10 cm.

*Color.*—RHS N77D.

Reproductive organs:

*Stamens.*—Not visible.

*Pollen amount.*—Absent.

*Pistil.*—Quantity: Many. Length: Less than 0.01 cm. Color: RHS N77D.

*Style.*—Not observed.

*Stigma.*—Shape: Ovoid. Diameter: Less than 0.01 cm. Color: RHS N77D.

*Ovary.*—Rarely visible.

*Ovary color.*—Not measured.

Fruit and seed set: None observed.

Disease and pest resistance: Not observed to date.

COMPARISON WITH PARENTAL AND COMMERCIAL VARIETIES

'ANTHEVEX' differs from the female parent plant 'ANTHUCOEN' (U.S. Plant Pat. No. 22,630) in that 'ANTHEVEX' has purple spathes and dark purple spadix, whereas 'ANTHUCOEN' has purple-red spathes and red spadix. Additionally, 'ANTHEVEX' has long-ovate leaves, whereas 'ANTHUCOEN' has deltoid leaves.

'ANTHEVEX' differs from the male parent plant '10441-14' (unpatented) in that 'ANTHEVEX' has purple spathes and dark purple spadix, whereas '10441-14' has purple-red spathes and dark purple-red spadix. Additionally, 'ANTHEVEX' has shorter spadix than '10441-14'.

'ANTHEVEX' differs from similar commercial variety 'ANTHDUBAQ' (U.S. Plant Pat. No. 27,889) in that 'ANTHEVEX' has long-ovate, purple spathes and green (RHS 144A) peduncles with RHS 187D toward the spathe, whereas 'ANTHDUBAQ' has cordate, red-purple spathes and green (RHS 144B) peduncles. Additionally, 'ANTHEVEX' is a shorter plant than 'ANTHDUBAQ'.

'ANTHEVEX' differs from similar commercial variety 'ANTHEBENEX' (unpatented) in that 'ANTHEVEX' long-ovate, purple spathes and green (RHS 144A) peduncles with RHS 187D toward the spathe, whereas 'ANTHEBENEX' has ovate, purple-red spathes and red-brown peduncles. Additionally, 'ANTHEVEX' is a shorter plant than 'ANTHEBENEX'.

I claim:

1. A new and distinct variety of *Anthurium* plant named 'ANTHEVEX', substantially as illustrated and described herein.

* * * * *